(12) United States Patent
Thomas

(10) Patent No.: US 6,373,040 B2
(45) Date of Patent: Apr. 16, 2002

(54) IN-CAVITY CONNECTORS FOR SYSTEM DETECTORS IN MICROWAVE ASSISTED PROCESSES

(75) Inventor: James Edward Thomas, Harrisburg, NC (US)

(73) Assignee: CEM Corporation, Matthews, NC (US)

( * ) Notice: Subject to any disclaimer, the term of this patent is extended or adjusted under 35 U.S.C. 154(b) by 0 days.

(21) Appl. No.: 09/874,638

(22) Filed: Jun. 5, 2001

Related U.S. Application Data

(62) Division of application No. 09/235,344, filed on Jan. 21, 1999.

(51) Int. Cl.[7] .................................................. H05R 6/80
(52) U.S. Cl. ....................................... 219/762; 219/679
(58) Field of Search ................................ 219/762, 679, 219/696, 698, 705, 704, 712, 750, 771; 422/90, 113; 324/767; 374/150; 202/176

(56) References Cited

U.S. PATENT DOCUMENTS

| | | | |
|---|---|---|---|
| 3,975,720 A | * 8/1976 | Chen et al. .................. 219/712 |
| 4,296,299 A | 10/1981 | Scottman et al. | |
| 4,632,127 A | 12/1986 | Sterzer | |
| 4,778,970 A | 10/1988 | Klaila | |
| 4,826,575 A | 5/1989 | Karamian et al. | |
| 5,049,816 A | 9/1991 | Moslehi | |
| 5,204,065 A | * 4/1993 | Floyd ......................... 422/113 |
| 5,206,479 A | 4/1993 | Zakaria et al. | |
| 5,230,865 A | 7/1993 | Hargett et al. | |
| 5,320,804 A | 6/1994 | Zakaria et al. | |
| 5,369,034 A | 11/1994 | Hargett et al. | |
| 5,427,741 A | 6/1995 | Bennett | |
| 5,443,795 A | * 8/1995 | Revesz ......................... 422/90 |
| 5,520,886 A | 5/1996 | Bennett et al. | |
| 5,988,877 A | * 11/1999 | Hochrad et al. ............ 374/150 |

FOREIGN PATENT DOCUMENTS

| | | |
|---|---|---|
| EP | 0 467 625 | 1/1992 |
| WO | WO99/13979 | 3/1999 |

* cited by examiner

*Primary Examiner*—Sang Paik
*Assistant Examiner*—Quang Van
(74) *Attorney, Agent, or Firm*—Summa & Allan, P.A.

(57) ABSTRACT

A system is disclosed for carrying out microwave assisted chemical reactions. The system includes a source of microwave radiation, a cavity in communication with the source, a plurality of reaction vessels in the cavity, a pressure line in fluid communication with at least one of the reaction vessels, a pressure transducer in communication with the pressure line, an electrical connector for the transducer in a wall of the cavity, and a shield around the connector that prevents microwaves launched into the cavity from interfering with electrical signals transmitted through the connector.

4 Claims, 1 Drawing Sheet

IN-CAVITY CONNECTORS FOR SYSTEM DETECTORS IN MICROWAVE ASSISTED PROCESSES

RELATED APPLICATION

This application is a divisional of Ser. No. 09/235,344 filed on Jan. 21, 1999.

FIELD OF THE INVENTION

The present invention relates to microwave assisted chemical processes, and in particular relates to processes carried out in closed vessels in microwave cavity resonators for which internal conditions in the vessels are preferably monitored.

BACKGROUND OF THE INVENTION

Microwave assisted chemistry refers to those techniques in which the initiation, acceleration, or other enhancement of an intended chemical reaction is encouraged by the application of microwave radiation to the chemical reaction. In many circumstances, where either reactants or the solutions or mixtures in which the reactants are found are susceptible to microwave radiation, the microwave radiation takes the place of conventional heating. For a number of reasons which are well understood and widely explained elsewhere, microwaves interact directly with such materials and thus tend to heat them much more quickly than other heating methods such as radiant conduction or convection heating. As a result, many chemical reactions can be carried out much more quickly in a microwave assisted environment than they can using conventional (e.g., conduction or convection) heating.

In addition to being enhanced by the application of microwaves, certain chemical reactions are preferably carried out under pressure. In many such circumstances, the reagents, solvents or other carriers generate the pressure as they evaporate into gases in a closed reaction vessel under the influence of the microwaves. When such reactions are being carried out, it is often desirable, and sometimes necessary, to monitor the temperature and pressure inside the vessel. Monitoring the temperature and pressure give a useful indication of the progress of certain reactions, can be used with feedback circuits and controllers to moderate the amount of microwave radiation being applied to a reaction, and in some cases, provide a necessary safety factor so that the application of microwaves can be stopped if pressure or temperature reach certain predetermined values.

One preferred method of measuring pressure in a reaction vessel during the application of microwaves is the use of a transducer type of sensor. Used in its broadest sense, the term "transducer" refers to a device which measures a primary signal and converts it into a secondary signal. The secondary signal is then used in a monitoring or control scheme. Pressure is considered to be a mechanical primary signal, although other primary signals can include thermal, electrical, magnetic, radiant, or even chemical signals. Because devices useful in microwave assisted chemistry are often used in conjunction with control circuits that include microprocessors, a preferred secondary signal from a transducer is an electrical signal. It will be recognized, however, that the secondary signal could also be mechanical, thermal, magnetic, radiant, or chemical in nature. For the sake of clarifying the discussions herein, the term "pressure transducer" will be primarily used to refer to a device in which the mechanical pressure exerted by the chemical reaction is translated into an electrical signal.

Because microwaves are electromagnetic radiation, however, they tend to interfere with the operation of electrical devices such as transducers. Alternatively, even if the microwaves don't interfere with the devices themselves, they may interfere with the signals generated by and transmitted from the transducer. Accordingly, in conventional microwave assisted chemical systems, the pressure transducer is typically located outside of the resonator cavity in which the reaction vessels are being exposed to the microwaves. In order to monitor the pressure, an appropriate pressure-resistant hose runs from the vessel, through the wall of the cavity, and then externally to the transducer.

Such arrangements of the vessel inside the cavity, the transducer outside the cavity, and the connecting pressure hose raises particular problems. First, the hose cannot be disconnected from the vessel or the transducer until the pressure in the vessel is otherwise released. Internal pressures in such reaction vessels often are quite high, in some cases 800 pounds per square inch (psi) or more. Theoretically, an in-cavity disconnect coupling of some type could be used a part of the pressure hose. Such a coupling would have to be both microwave-transparent while sufficiently strong to withstand the high pressures. To date, however, such couplings are either unavailable, too inconvenient for reasonable use (e.g., size and positioning problems), or so expensive as to be commercially unreasonable with respect to the overall cost of the device.

Accordingly, in commercial devices, the transducer must be maintained on the outside, and the vessels cannot be disconnected from the transducer until they have cooled sufficiently to reduce the pressure in the vessels to manageable and safe levels. As a result, although microwaves can accelerate certain reactions to completion relatively quickly, the cooling down and depressurization of the vessels can take a disproportionately long time, thus slowing down the overall turnaround rate of the reactions. Because one advantage of microwave assisted chemistry is its enhanced speed, the requirement of waiting for vessels to cool and depressurize moderates some of that advantage. For example, many laboratory microwave devices hold six or more of the high pressure reaction vessels, so that six or more reactions (usually with identical reagents) can be carried out at the same time. These devices can be used repeatedly to run dozens of tests in a relatively short time, except for the down time required for one set of vessels to cool before they can be disconnected and removed from the microwave cavity.

Accordingly, a need exists for an apparatus in which vessels can be removed from the cavity while still hot and under high pressure, but without having to disconnect them from the transducer while the transducer is being exposed to the high pressure from the vessels.

OBJECT AND SUMMARY OF THE INVENTION

Therefore, it is an object of the present invention to provide a system and apparatus in which pressure vessels can be removed from a microwave cavity while they are still under pressure and while they are still connected to a transducer.

The invention meets this object with a detection vessel for use in carrying out microwave assisted chemical reactions. The detection vessel comprises a body formed of a material that is substantially transparent to microwave radiation; a sensor that converts a primary signal from inside the vessel into an electrical signal; an electrical connector for the sensor; and a grounded shield around the connector for preventing microwaves from interfering with electrical signals transmitted through the connector.

In another aspect, the invention is a system for carrying out microwave assisted chemical reactions. The system comprises a microwave resonator cavity, an electrical connector in the cavity, and a grounded shield around the connector that prevents microwaves launched into the cavity from interfering with electrical signals transmitted through the connector.

The foregoing and other objects and advantages of the invention will become more clear when taken in conjunction with the Detailed Description and the accompanying drawings in which:

DETAILED DESCRIPTION OF THE PREFERRED EMBODIMENTS

Figure 1:
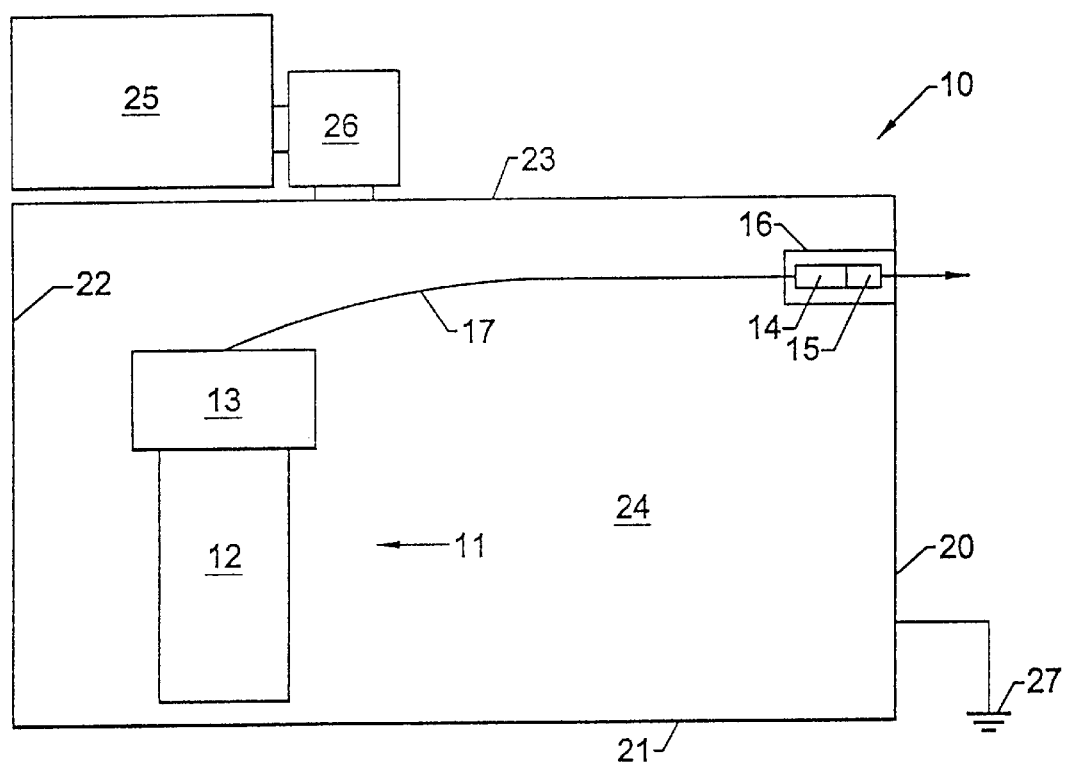
FIG. 1 is a schematic diagram of the relationship between a cavity, pressure vessel, pressure hose, transducer, connector, and shield according to the present invention.

The present invention is a system for carrying out microwave assisted chemical reactions. The system is broadly designated at 10 in FIG. 1. In its broadest sense, the invention is a reaction vessel broadly designated at 11 in FIG. 1 for use in carrying out microwave assisted chemical reactions. The detection vessel comprises a body 12 that is formed of a material that is substantially transparent to microwave radiation. As schematically illustrated in FIG. 1, the body portion further includes a pressure sealing cap 13 that can be removed in order to provide a relatively wide mouth to the body 12 into which reagents can be placed. The particular design and features (other than the invention) of the vessel 11 can be conventional in this art with exemplary vessels being set forth, for example, in commonly assigned U.S. Pat. Nos. 5,206,479; 5,230,865; 5,320,804; 5,369,034; 5,427,741; and 5,520,886; the contents of which are incorporated entirely herein by reference. The vessel includes a sensor shown as the transducer 14 that converts a primary signal from inside the vessel into an electrical signal. The sensor is connected to an electrical connector 15, and a grounded shield 16 is positioned around the connector 15 for preventing microwaves from interfering with electrical signals transmitted through the connector.

In the preferred embodiments and as illustrated in FIG. 1, the sensor comprises a pressure hose 17 in communication with the interior of the vessel 11 with the sensor 14 comprising a pressure transducer in fluid communication with the hose 17 and in electrical communication with the shielded connector 15. The operation of such sensors, including pressure transducers, is well-understood by those of ordinary skill in this art, and an appropriate discussion is also set forth in Dorf, *The Electrical Engineering Handbook*, Second Ed. (1997, CRC Press) at Chapter 56, "Sensors," at page 1255ff. Appropriate pressure transducers are commercially available from numerous sources, including (by way of example and not limitation), Entran Devices, Inc., 10 Washington Ave., Fairfield, N.J. 07004.

The connector 15 is selected to be functionally compatible with the sensor 14, and as such can be selected by those or ordinary skill in this art and without undue experimentation. Many types of appropriate connectors are commercially available, with AMP Inc. (Harrisburg, Pa.) being an exemplary (but not sole) source of almost any type of electrical connector desired or necessary.

In these preferred embodiments, the hose 17 is preferably substantially transparent to microwave radiation, and the shield 16 is positioned in and grounded by one wall 20 of a microwave resonator cavity that is schematically defined by a plurality of walls, of which the wall 20 and corresponding walls 21, 22, and 23 are illustrated in FIG. 1. The cavity defined by the walls is designated at 24 in FIG. 1. For a number of reasons, including minimizing or eliminating interference with microwave radiation in the cavity, the shield 16 is made of metal and is preferably cylindrical in shape. The shape of the transducer 14 (i.e., its external housing) is less critical once it has been shielded, but is often cylindrical as is the connector 15.

As noted above, the shield 16 is preferably grounded by the wall 20. The cavity walls, including the grounding wall 20, are formed of a material, usually metal, that reflects (rather than transmits) of microwave energy. In turn, the metal grounding wall 20 can itself be grounded by any appropriate arrangement. Appropriate grounding techniques and structures are well known in the art and will not be otherwise discussed herein.

Accordingly, in another aspect, the invention comprises an entire system for carrying out microwave assisted chemical reactions. In this aspect, the invention comprises the microwave resonator cavity 24, the electrical connector 15 in the cavity 24, and the grounded shield 16 around the connector 15 that prevents microwaves launched into the cavity from interfering with electrical signals transmitted through the connector 15. As noted above, the cavity 24 is defined by the plurality of walls, including, but not limited to, the walls 20, 21, 22, and 23 illustrated in FIG. 1. In this embodiment, the shield 16 is again positioned in the cavity wall 20 which in turn is electrically grounded at 27 to thus electrically ground the shield. FIG. 1 also shows that the system comprises a source of microwave radiation schematically indicated as the magnetron 25 in FIG. 1, and means for launching the radiation from the source into the cavity. The launching means can include a waveguide 26, the operation and design of which are well know to those of ordinary skill in this art. An overall discussion of microwave propagation, including waveguides and resonator cavities, is likewise set forth in Dorf, supra, at Chapter 39, "Microwave Devices," pages 979ff.

Similarly, principles of shielding are generally well understood in this art. The shield 16 is selected and designed to prevent microwaves in the cavity from affecting either the operation of the transducer 14, or the electrical signals generated by the transducer 14 and transmitted therefrom. Dorf, supra, at Chapter 40, "Compatibility," pages 1003ff, gives an appropriate overall discussion of basic grounding and shielding principles.

The microwave source 25 is usually a magnetron because of its well-understood operation, generally wide availability, and proportionally reasonable cost. The source 25 could also include other devices, however, such as klystrons, solid state devices, or other particular devices such as that set forth in co-pending and commonly assigned U.S. U.S. application Ser. No. 09/063,545, filed Apr. 21, 1998, to Greene et al. for "Use of Continuously Variable Power in Microwave Assisted Chemistry," the contents of which are incorporated entirely herein by reference.

In the preferred embodiments, the grounded shield 16 is also of a size and shape sufficient to act as a microwave choke. As known to those familiar with the propagation of microwave radiation, the size of the choke is selected based upon the wavelength and frequency of the propagated microwaves. Thus, those of ordinary skill in this art can select a choke of an appropriate size without undue experimentation. By way of example and not limitation, however, for a typical microwave frequency of 2450 MHZ, the shield 16 will comprise a cylinder having dimensions of about 2 inches in length and 0.8 inch in diameter to also act as an appropriate choke.

As set forth above, in preferred embodiments, the sensor 14 comprises a pressure transducer in electrical communication with the connector 15 for converting a primary signal into an electrical signal.

In yet another embodiment, the invention comprises a source of microwave radiation shown as the magnetron 25, a cavity 24 in communication (i.e., microwave communication) with the magnetron 25, a reaction vessel 11 in the cavity 24, a sensor associated with the vessel 11 for measuring a physical parameter within the vessel 11, an electrical connector 15 for the sensor adjacent a wall 20 of the cavity 24, and a shield 16 around the connector that prevents microwaves launched into the cavity from interfering with electrical signals transmitted through the connector. The sensor preferably converts a physical characteristic of the contents of the reaction vessel 11 into an electrical signal, and in the most preferred embodiments the sensor comprises a pressure line 17 in fluid communication with the reaction vessel 11, and a pressure transducer 14 in communication with the pressure line 17. In the preferred embodiments, the transducer 14 is also surrounded by and thus shielded by the grounded shield 16 which is in electrically grounding contact with the wall 20. As in the previous embodiments, the grounded shield also comprises a microwave choke so that the arrangement of the shield, the transducer and the connector 15 prevents microwaves from leaking from the cavity 24.

In each case, the shield 16 needs to be grounded to avoid interfering with or being undesirably affected by the microwaves in the cavity 24. Although the shield 16 could be grounded in some manner other than in contact with a metal wall, such an arrangement would require an additional grounding wire in the cavity 24. Although the use of such a grounding wire is not impossible, it does offer certain disadvantages in some circumstances because if of a sufficient length or diameter (or both), it can act as an antenna for the propagated microwaves. Thus, the shield 16 is most preferably positioned against and grounded by the wall 20. When not grounded by the wall 20, the shield 16 must be grounded in some manner that is appropriately kept from interfering with the propagated microwaves. In turn, when the shield 16 is placed against the wall 20, it could provide an opening through which microwaves can escape, and thus is preferably of a size and shape that will act as the microwave choke as noted above.

In a most preferred embodiment of the invention, the system comprises a plurality of reaction vessels in the cavity 24. Such an arrangement is similarly disclosed in a number of the above-referenced commonly assigned prior patents including for example U.S. Pat. Nos. 5,206,479 and 5,320,804. In such circumstances, usually one of the vessels is monitored while the remained are assumed to have conditions therein similar to the one being monitored.

In use, the system permits the transducer 14 to be disengaged from the connector 15 while the reaction vessel 11 remains sealed and under pressure. As a result, the vessel 11, and any others, can be removed from the cavity 24 as soon as a reaction is completed (or at any other desired point). In turn, a new vessel or set of vessels can immediately be placed in the cavity and then subjected to microwave radiation without waiting for a previous set to cool and depressurize. The system thus permits a faster and more efficient use of the available microwave equipment.

In the drawings and specification, there have been disclosed typical embodiments of the invention, and, although specific terms have been employed, they have been used in a generic and descriptive sense only and not for purposes of limitation, the scope of the invention being set forth in the following claims.

That which is claimed is:

1. A detection vessel for use in carrying out microwave assisted chemical reactions, said detection vessel comprising:
    a body formed of a material that is substantially transparent to microwave radiation;
    a sensor that converts a primary signal from inside said vessel into an electrical signal;
    an electrical connector for said sensor;
    a transducer adjacent said electrical connector; and
    a shield around said connector and transducer, said shield being positioned in and grounded by the walls of a microwave resonator cavity for preventing microwaves from interfering with electrical signals transmitted through said connector.

2. A detection vessel according to claim 1 wherein said sensor comprises a pressure hose in fluid communication with the interior of said vessel; and wherein said transducer is a pressure transducer in fluid communication with said hose, and in electrical communication with said shielded connector.

3. A detection vessel according to claim 2 wherein said pressure hose is substantially transparent to microwave radiation.

4. A detection vessel according to claim 3 wherein said shield has a size and shape sufficient to serve as a microwave choke.

* * * * *